United States Patent
Yoon et al.

(10) Patent No.: US 11,331,025 B2
(45) Date of Patent: May 17, 2022

(54) DROWSY-DRIVING PREVENTION METHOD AND DROWSY-DRIVING PREVENTION SYSTEM

(71) Applicant: LG ELECTRONICS INC., Seoul (KR)

(72) Inventors: Hee Nam Yoon, Seoul (KR); Beom Oh Kim, Suwon-si (KR)

(73) Assignee: LG ELECTRONICS INC., Seoul (KR)

( * ) Notice: Subject to any disclaimer, the term of this patent is extended or adjusted under 35 U.S.C. 154(b) by 371 days.

(21) Appl. No.: 16/542,251

(22) Filed: Aug. 15, 2019

(65) Prior Publication Data
US 2020/0037945 A1 Feb. 6, 2020

(30) Foreign Application Priority Data

Jul. 11, 2019 (KR) .......................... 10-2019-0083903

(51) Int. Cl.
*A61B 5/18* (2006.01)
*B60W 40/08* (2012.01)
(Continued)

(52) U.S. Cl.
CPC .............. *A61B 5/18* (2013.01); *A61B 5/0051* (2013.01); *A61B 5/0533* (2013.01);
(Continued)

(58) Field of Classification Search
None
See application file for complete search history.

(56) References Cited

U.S. PATENT DOCUMENTS

| 2012/0066011 A1* | 3/2012 | Ichien | B60W 40/09 705/4 |
| 2013/0226408 A1* | 8/2013 | Fung | B62D 6/007 701/41 |

(Continued)

FOREIGN PATENT DOCUMENTS

| JP | H07244787 | 9/1995 |
| JP | 2008049067 | 3/2008 |

(Continued)

OTHER PUBLICATIONS

Korean Intellectual Property Office Application No. 10-2019-0083903, Office Action dated Nov. 17, 2020, 8 pages.

(Continued)

*Primary Examiner* — Thomas S McCormack
(74) *Attorney, Agent, or Firm* — Lee, Hong, Degerman, Kang & Waimey PC

(57) ABSTRACT

Disclosed herein are a drowsy-driving prevention method and a drowsy-driving prevention system that execute artificial intelligence (AI) algorithms and/or machine learning algorithms in a 5G environment connected for Internet of Things in order to control a stimulation unit and a measurement unit. The drowsy-driving prevention method may include a stimulating step, a measuring step, and a determining step. A stimulation unit outputs a stimulus in order to stimulate a sensory organ of a driver, and then a measurement unit measures a biometric signal of the driver from the time when the stimulus is outputted. Upon determining that the biometric signal of the driver is not a response to the stimulus, the stimulation unit may output the stimulus again.

5 Claims, 7 Drawing Sheets

(51) Int. Cl.
    *B60Q 9/00*       (2006.01)
    *A61B 5/0533*     (2021.01)
    *A61B 5/00*       (2006.01)
    *B62D 1/04*       (2006.01)
(52) U.S. Cl.
    CPC .............. *A61B 5/6893* (2013.01); *B60Q 9/00* (2013.01); *B60W 40/08* (2013.01); *B60W 2040/0827* (2013.01); *B60W 2040/0872* (2013.01); *B60W 2540/26* (2013.01); *B62D 1/046* (2013.01)

(56) References Cited

U.S. PATENT DOCUMENTS

| | | | | |
|---|---|---|---|---|
| 2018/0141570 A1* | 5/2018 | Kimura | ................. | B60W 50/16 |
| 2019/0161091 A1* | 5/2019 | An | ..................... | B60W 50/085 |
| 2019/0389455 A1* | 12/2019 | Reed | ..................... | B60W 30/09 |

FOREIGN PATENT DOCUMENTS

| | | |
|---|---|---|
| JP | 2010008268 | 1/2010 |
| KR | 1020070093201 | 9/2007 |
| KR | 101828067 | 2/2018 |
| KR | 102018117961 | 10/2018 |
| KR | 1020180117961 | 10/2018 |

OTHER PUBLICATIONS

Korean Intellectual Property Office Application No. 10-2019-0083903, Office Action dated May 6, 2020, 8 pages.

\* cited by examiner

DROWSY-DRIVING PREVENTION METHOD AND DROWSY-DRIVING PREVENTION SYSTEM

CROSS-REFERENCE TO RELATED APPLICATION

Pursuant to 35 U.S.C. § 119(a), this application claims the benefit of earlier filing date and right of priority to Korean Patent Application No. 10-2019-0083903, filed on Jul. 11, 2019, the contents of which are all hereby incorporated by reference herein in its entirety.

BACKGROUND

1. Technical Field

The present disclosure relates to a drowsy-driving prevention method and a drowsy-driving prevention system, and more particularly to a drowsy-driving prevention method and a drowsy-driving prevention system that are capable of recognizing a drowsy state of a vehicle driver and changing the state of the driver to an aroused state.

2. Description of Related Art

A representative problem caused due to an increase in use of vehicles is a traffic accident. In particular, the major cause of traffic accidents on large highways, which may lead to heavy damage, is drowsy driving. For this reason, much research to prevent drowsy driving has been conducted.

In connection therewith, Korean Patent Application Publication No. 2007-0093201 (hereinafter referred to as "Related Art 1") discloses a device for sensing a biometric signal of a driver. According to the disclosure in Related Art 1, the sensing device includes a detection unit, a data processing unit, a data line, and a recording unit.

According to the disclosure in Related Art 1, a galvanic skin response (GSR) sensor, a body temperature sensor, a heart rate sensor, and a pressure sensor are installed at the surface of a steering wheel in order to continuously detect the biometric signal of the driver. The detected biometric signal of the driver is recorded in the recording unit. Data recorded in the recording unit are used for research to prevent and warn the driver of drowsy driving, to analyze a traffic accident, and to control the interior environment of a vehicle. In the case in which it is suspected that the driver is performing drowsy driving, as the result of comparing the measured biometric signal with a predetermined signal, the temperature in the vehicle may be adjusted or a warning sound may be outputted.

Korean Patent Registration No. 1828067 (hereinafter referred to as "Related Art 2") discloses a wrist band for monitoring the state of a vehicle driver. According to the disclosure in Related Art 2, the biometric state of the driver during driving is monitored in real time through sensors such as a GSR sensor, an electrocardiogram (ECG) sensor, and a biometric impedance sensor installed at the wrist band. Upon determining, as the result of monitoring, that the driver is performing drowsy driving, the wrist band is vibrated in order to prevent the occurrence of an accident.

However, body temperature, heart rate, and GSR show deviation for each subject. In addition, for the same subject, there is deviation depending on the ambient temperature, the health state, and a change in the emotion of the subject when measurement is performed. Furthermore, the body temperature, the heart rate, and the GSR are characterized as gradually increasing at the boundary between an aroused state and a drowsy state. In the case of Related Art 1 and Related Art 2, therefore, it is difficult to rapidly and accurately distinguish between the aroused state and the drowsy state merely through analysis of change patterns of the body temperature, the heart rate, and the GSR.

Also, in the case in which the driver is in a shallow sleep state, the driver may be awakened through adjustment of interior temperature, outputting of a warning sound, or generation of vibration. In the case in which the driver is in a deep sleep state, however, there is a danger of the driver continuing to be in a sleep state even though the interior temperature has been adjusted, the warning sound has been outputted, or the vibration has been generated.

RELATED ART DOCUMENTS

Korean Patent Application Publication No. 2007-0093201 (Publication Date: Sep. 18, 2007)

Korean Patent Registration No. 1828067 (Registration Date: Feb. 5, 2018)

SUMMARY OF THE INVENTION

The present disclosure is directed to providing a drowsy-driving prevention method and a drowsy-driving prevention system that are capable of improving quickness and accuracy in detecting drowsy-driving based on the measurement of a biometric signal.

The present disclosure is further directed to providing a drowsy-driving prevention method and a drowsy-driving prevention system that are capable of rapidly changing the state a driver to an aroused state, from a deep sleep state as well as a shallow sleep state.

The present disclosure still further directed to providing a drowsy-driving prevention method and a drowsy-driving prevention system that are capable of addressing the issue in the related art described above in which there is inaccuracy in detecting drowsy driving due to deviation in biometric signals for each subject and deviation in biometric signals depending on a change in an ambient environment and an emotional state.

A drowsy-driving prevention system according to an embodiment of the present disclosure may include a stimulation unit, a measurement unit, and a controller.

The stimulation unit may output a stimulus in order to stimulate a sensory organ of a driver.

The measurement unit may measure a biometric signal of the driver from the time when the stimulus is outputted.

The controller may control the stimulation unit and the measurement unit, and may determine whether the biometric signal of the driver is a response to the stimulus.

The stimulation unit may be a vibration device, and the measurement unit may be a GSR measurement device.

The stimulation unit and the measurement unit may be mounted to a steering wheel of a vehicle.

A drowsy-driving prevention method according to another embodiment of the present disclosure may include a stimulating step, a measuring step, and a determining step.

At the stimulating step, a stimulation unit may output a stimulus in order to stimulate a sensory organ of a driver.

At the measuring step, a measurement unit may measure a biometric signal of the driver from the time when the stimulus is outputted.

At the determining step, it may be determined whether the biometric signal of the driver is a response to the stimulus.

Upon determining that the biometric signal of the driver is not a response to the stimulus, the stimulating step may be reperformed.

The controller may store determination reference information used to determine whether the biometric signal of the driver is a response to the stimulus.

When the determining step is completed, the determination reference information may be updated so as to include information determined at the determining step.

A capture unit for capturing an image of the driver may be further provided in a vehicle.

The drowsy-driving prevention method may further include a step of recognizing the driver by analyzing the image captured by the capture unit.

The determination reference information may be updated for each driver.

At least one measurement sensor selected from among an illuminance sensor, a temperature sensor, and a carbon dioxide sensor may be provided in the interior of the vehicle.

When the determining step is completed, the determination reference information may be updated so as to include information determined at the determining step and information measured by the measurement sensor.

A drowsy-driving prevention method according to still another embodiment of the present disclosure may include a stimulating step, a measuring step, a determining step, and a confirming step.

At the stimulating step, a stimulation unit may output a stimulus in order to stimulate a sensory organ of a driver.

At the measuring step, a measurement unit may measure a biometric signal of the driver from the time when the stimulus is outputted.

At the determining step, it may be determined whether the biometric signal of the driver is a response to the stimulus.

At the confirming step, it may be confirmed whether the driver is performing drowsy driving by analyzing the image captured by the capture unit, upon determining that the biometric signal of the driver is not a response to the stimulus.

Upon determining that the driver is performing drowsy driving, the stimulating step may be reperformed.

A drowsy-driving prevention method according to a yet another embodiment of the present disclosure may include a first stimulating step, a first measuring step, a first determining step, a second stimulating step, a second measuring step, and a second determining step.

At the first stimulating step, a stimulation unit may output a first stimulus in order to stimulate a sensory organ of a driver.

At the first measuring step, a measurement unit may measure a biometric signal of the driver from the time when the first stimulus is outputted.

At the first determining step, it may be determined whether the biometric signal of the driver is a response to the first stimulus.

At the second stimulating step, the stimulation unit may output a second stimulus in order to stimulate the sensory organ of the driver upon determining that the biometric signal of the driver is not a response to the first stimulus.

At the second measuring step, the measurement unit may measure a biometric signal of the driver from the time when the second stimulus is outputted.

At the second determining step, it may be determined whether the biometric signal of the driver is a response to the second stimulus.

Upon determining that the biometric signal of the driver is not a response to the second stimulus, the second stimulating step may be reperformed.

The first stimulus and the second stimulus may stimulate different sensory organs of the driver.

The second stimulus may stimulate the same sensory organ of the driver with higher intensity than the first stimulus.

The intensity or pattern of the second stimulus may be changed whenever the second stimulating step is reperformed.

Upon determining that the measured biometric signal of the driver is not a response to the stimulus, the autonomous driving level of the vehicle may be increased. In the case in which the autonomous driving level is increased, an accident of the vehicle may be prevented before the state of the driver is changed from a drowsy state to an aroused state. Upon determining that the state of the driver has changed from a drowsy state to an aroused state, the autonomous driving level of the vehicle may be decreased to the original state thereof.

A computer program according to an embodiment of the present disclosure may be configured to be stored in a recording medium readable by a computer in order to perform a drowsy-driving prevention method using the computer.

According to embodiments of the present disclosure, it is possible to provide a drowsy-driving prevention method and a drowsy-driving prevention system that are capable of stimulating a sensory organ of a driver, measuring a biometric signal of the driver, and determining whether the biometric signal is a response to the stimulus, thereby improving quickness and accuracy in detecting drowsy-driving based on the measurement of the biometric signal.

According to embodiments of the present disclosure, it is possible to provide a drowsy-driving prevention method and a drowsy-driving prevention system that are capable of stimulating different sensory organs of a driver using a first stimulus and a second stimulus, stimulating the same sensory organ of the driver using the second stimulus having higher intensity than the first stimulus, or changing the intensity or pattern of the second stimulus whenever a second stimulating step is reperformed, thereby rapidly changing the state of the driver to an aroused state, from a deep sleep state as well as from a shallow sleep state.

According to embodiments of the present disclosure, it is possible to provide a drowsy-driving prevention method and a drowsy-driving prevention system that are capable of updating determination reference information so as to include information determined in a determining step and information measured by a sensor, and updating the determination reference information for each driver, thereby addressing the issue in the related art described above in which there is inaccuracy in detecting drowsy driving due to deviation in biometric signals for each subject and deviation in biometric signals depending on a change in an ambient environment and an emotional state.

BRIEF DESCRIPTION OF THE DRAWINGS

The above and other aspects, features, and advantages of the present disclosure will become apparent from the detailed description of the following aspects in conjunction with the accompanying drawings, in which.

DETAILED DESCRIPTION

Figure 1:
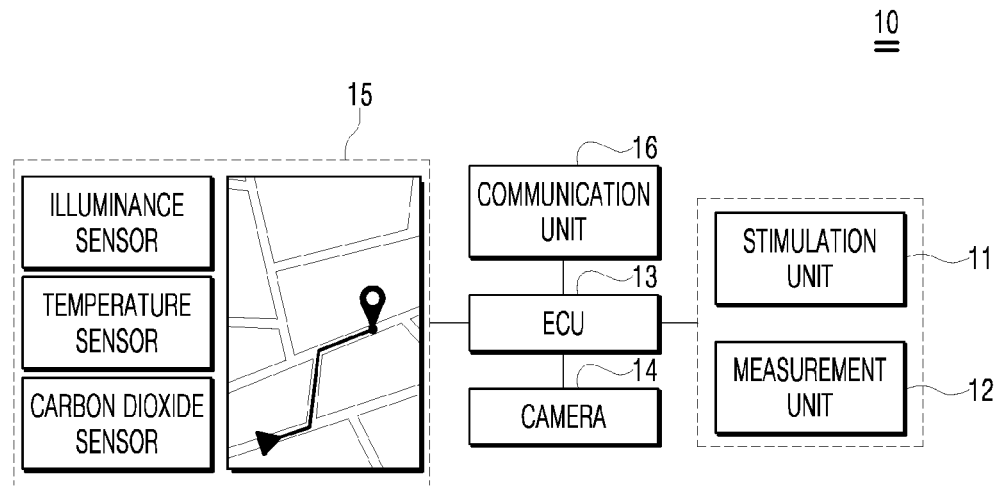
FIG. 1 is a schematic diagram showing a drowsy-driving prevention system according to an embodiment of the present disclosure.

Advantages and features of the present disclosure and methods of achieving the advantages and features will be more apparent with reference to the following detailed description of example embodiments in connection with the accompanying drawings. However, the description of particular example embodiments is not intended to limit the present disclosure to the particular example embodiments disclosed herein, but on the contrary, it should be understood that the present disclosure is to cover all modifications, equivalents and alternatives falling within the spirit and scope of the present disclosure.

The example embodiments disclosed below are provided so that the present disclosure will be thorough and complete, and also to provide a more complete understanding of the scope of the present disclosure to those of ordinary skill in the art. In the interest of clarity, not all details of the relevant art are described in detail in the present specification in so much as such details are not necessary to obtain a complete understanding of the present disclosure.

The terminology used herein is used for the purpose of describing particular example embodiments only and is not intended to be limiting. As used herein, the singular forms complete understanding of the present disclosure to include the plural forms as well, unless the context clearly indicates otherwise. The terms "comprises," "comprising," "includes," "including," "containing," "has," "having" or other variations thereof are inclusive and therefore specify the presence of stated features, integers, steps, operations, elements, and/or components, but do not preclude the presence or addition of one or more other features, integers, steps, operations, elements, components, and/or groups thereof. Furthermore, the terms such as "first," "second," and other numerical terms may be used herein only to describe various elements, but these elements should not be limited by these terms. Furthermore, these terms such as "first," "second," and other numerical terms, are used only to distinguish one element from another element.

Hereinbelow, the example embodiments of the present disclosure will be described in greater detail with reference to the accompanying drawings, and on all these accompanying drawings, the identical or analogous elements are designated by the same reference numeral, and repeated description of the common elements will be omitted.

Figure 2:
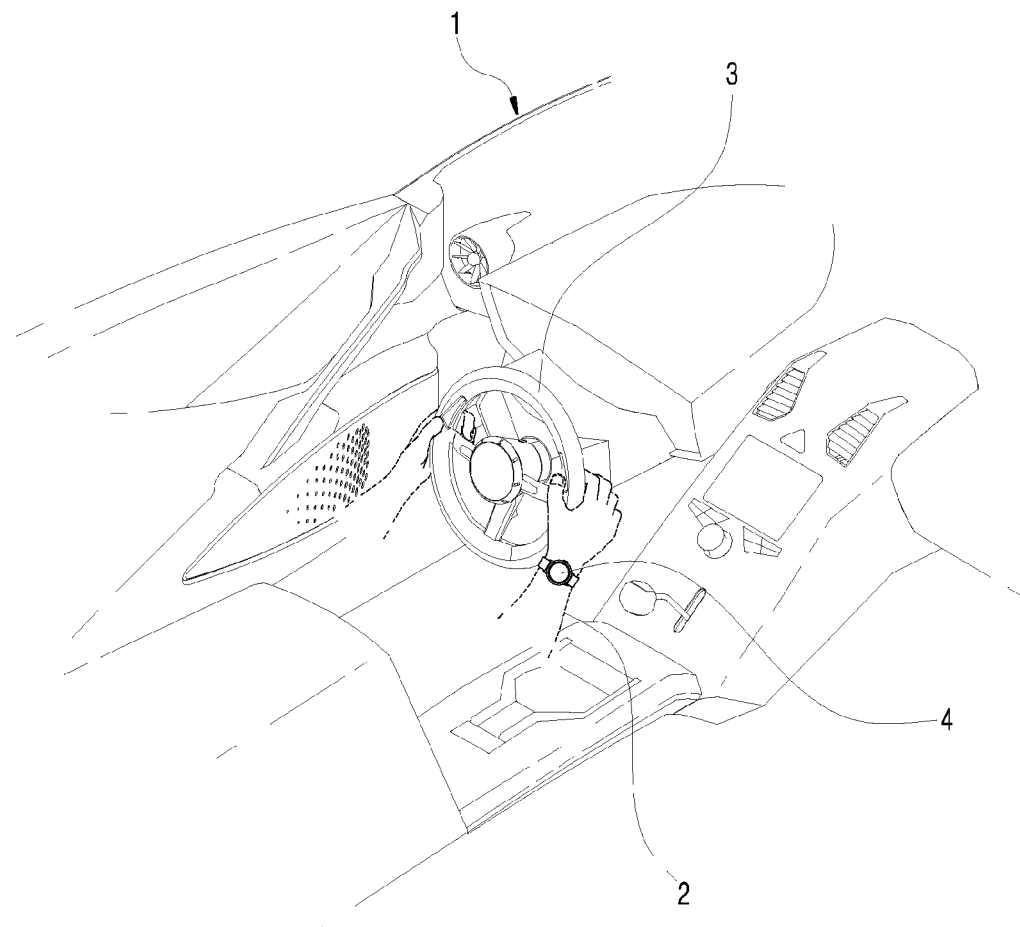
FIG. 2 is a diagram showing a vehicle equipped with the drowsy-driving prevention system of FIG. 1.

FIG. 1 is a schematic diagram showing a drowsy-driving prevention system 10 according to an embodiment of the present disclosure, and FIG. 2 is a diagram showing a vehicle 1 equipped with the drowsy-driving prevention system 10 of FIG. 1.

As shown in FIGS. 1 and 2, the drowsy-driving prevention system 10 according to the embodiment of the present disclosure includes a stimulation unit 11, a measurement unit 12, and a controller 13.

The stimulation unit 11 is a component that outputs a stimulus in order to stimulate a sensory organ of a driver 2. Here, the stimulus generally refers to changing at least one of visual sensation, auditory sensation, olfactory sensation, gustatory sensation, or tactile sensation. The stimulus may be transmitted to the sensory organ of the driver 2 through, for example, an image, sound, smell, taste, wind, or vibration.

The stimulation unit 11 may be configured as at least one of a vibration device that generates vibration, an audio device, a video device, or an air conditioning device. The stimulation unit 11 may be configured as a vibration device installed at a steering wheel 3.

A drowsy-driving prevention method (S100) according to an embodiment of the present disclosure will be described on the assumption that the stimulation unit 11 may be configured as a vibration device installed at the steering wheel 3. The vibration device installed at the steering wheel 3 is disclosed in Korean Patent Registration No. 1721724, and therefore a detailed description thereof will be omitted.

The measurement unit 12 is a component that measures a biometric signal of the driver 2 from the time when the stimulus is outputted. The measurement unit 12 may be configured as a galvanic skin response (GSR) measurement device, a temperature measurement device, or a heart rate measurement device.

The drowsy-driving prevention method (S100) according to an embodiment of the present disclosure will be described on the assumption that the measurement unit 12 is configured as a GSR sensor. The SGR sensor may be installed at the steering wheel 3 or in a watch 4. The SGR sensor installed at the steering wheel 3 is disclosed in Korean Patent Application Publication No. 2007-0093201, and therefore a detailed description thereof will be omitted.

Galvanic skin response is an electrical response generated in the skin depending on arousal levels. Arousal means the state in which various nerves are physiologically active. Arousal is lowest in a sleeping state.

Galvanic skin response increases or decreases depending on an increase or decrease in stress or arousal levels. GSR is a physiological signal that is sensitive to the arousal levels. GSR is used as an objective indicator of the mental state of a person, since the GSR is capable of being measured as a relatively stable index.

The controller 13 is a component that controls the stimulation unit 11 and the measurement unit 12. Here, the controller 13 may include all kinds of devices that are capable of processing data, such as a processor. Here, the 'processor' may refer to a data processing device built in a hardware, which includes physically structured circuits in order to perform functions represented as a code or command present in a program.

Examples of the data processing device built in a hardware include, but are not limited to, processing devices such as a microprocessor, a central processing unit (CPU), a processor core, a multiprocessor, an application-specific integrated circuit (ASIC), a field programmable gate array (FPGA), and the like.

In this embodiment, the drowsy-driving prevention system 10 may perform machine learning, such as deep learning, with respect to whether a response pattern to the stimulus appears in the measured biometric signal of the driver 2.

The drowsy-driving prevention system 10 may include a storage unit. The storage unit may store data used for machine learning, result data, and the like. In addition, the storage unit may temporarily or permanently store data processed by the controller 13.

Here, the storage unit may include magnetic storage media or flash storage media. However, the present disclosure is not limited thereto.

The storage unit may include an internal memory and/or an external memory, and may include a volatile memory, such as DRAM, SRAM, or SDRAM, a nonvolatile memory, such as one time programmable ROM (OTPROM), PROM, EPROM, EEPROM, mask ROM, flash ROM, a NAND flash memory, or a NOR flash memory, a flash drive, such as an SSD, a compact flash (CF) card, an SD card, a Micro-SD card, a Mini-SD card, an Xd card, or a memory stick, or a storage device, such as an HDD.

Deep learning, which is a subfield of machine learning, enables data-based learning through multiple layers. As the number of layers in deep learning increases, the deep learning network may acquire a collection of machine learning algorithms that extract core data from multiple datasets.

Deep learning structures may include an artificial neural network (ANN), and may include a convolutional neural network (CNN), a recurrent neural network (RNN), a deep belief network (DBN), and the like.

The deep learning structure according to the present embodiment may use various structures well known in the art. For example, the deep learning structure according to the present disclosure may include a CNN, an RNN, a DBN, and the like. RNN is an artificial neural network structure which is formed by building up layers at each instance, and which is heavily used in natural language processing and the like and effective for processing time-series data which vary over a course of time.

A DBN includes a deep learning structure formed by stacking up multiple layers of a deep learning scheme, restricted Boltzmann machines (RBM). A DBN has the number of layers formed by repeating RBM training.

A CNN includes a model mimicking a human brain function, built under the assumption that when a person recognizes an object, the brain extracts the most basic features of the object and recognizes the object based on the results of complex processing in the brain.

Meanwhile, the artificial neural network can be trained by adjusting connection weights between nodes (if necessary, adjusting bias values as well) so as to produce desired output from given input.

Also, the artificial neural network can continuously update the weight values through learning. Furthermore, methods such as back propagation may be used in training the artificial neural network.

Meanwhile, the drowsy-driving prevention system 10 may be equipped with an artificial neural network, and may perform a machine-learning-based determining step of determining whether a response pattern to the stimulus appears in the measured biometric signal of the driver 2.

The controller 13 may include an artificial neural network, for example, a deep neural network (DNN), such as a CNN, an RNN, and a DBN, and may train the deep neural network. Both unsupervised learning and supervised learning may be used as a machine learning method of the artificial neural network.

Figure 3:
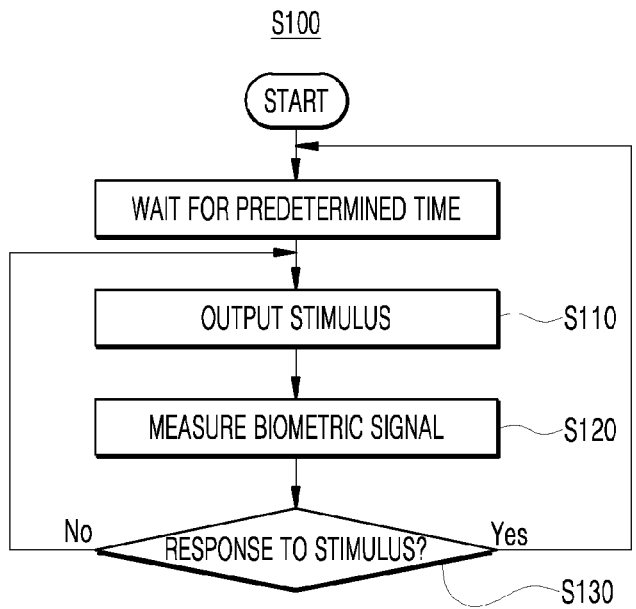
FIG. 3 is a flowchart showing a drowsy-driving prevention method according to a first embodiment of the present disclosure.
Figure 4A:
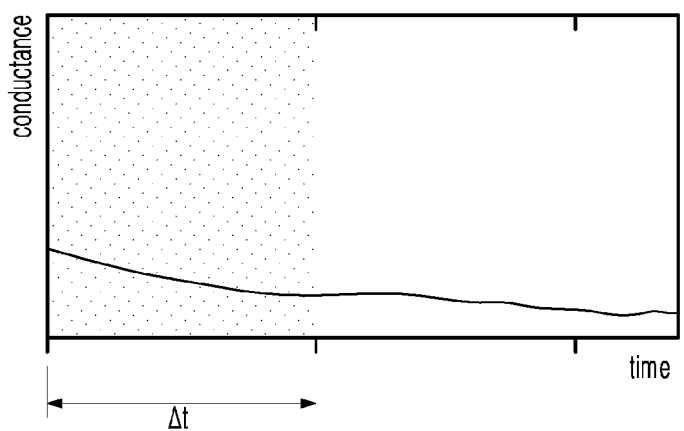
FIGS. 4A and 4B are graphs showing a driver's biometric signal measured at a measuring step.
Figure 4B:
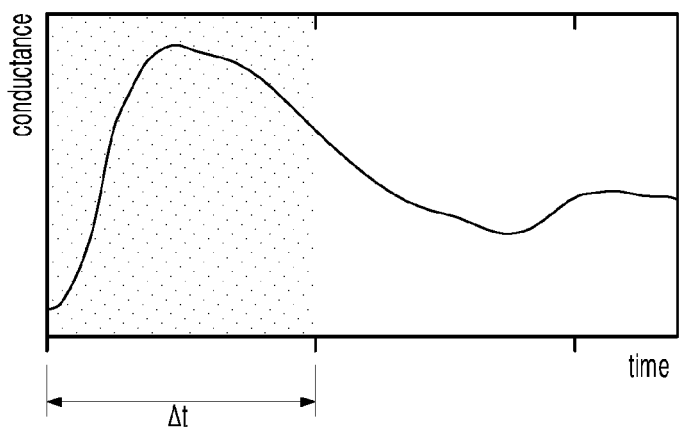

FIG. 3 is a flowchart showing a drowsy-driving prevention method (S100) according to a first embodiment of the present disclosure, and FIGS. 4A and 4B are graphs showing a biometric signal of the driver 2 measured at a measuring step (S120).

As shown in FIG. 3, the drowsy-driving prevention method (S100) according to the first embodiment of the present disclosure may include a stimulating step (S110), a measuring step (S120), and a determining step (S130).

The stimulating step (S110) is a step of the stimulation unit 11 outputting a stimulus. Referring to FIG. 2, the stimulation unit 11 may be configured as a vibration device installed at the steering wheel 3.

The stimulating step (S110) is automatically commenced a predetermined time after the vehicle 1 is started. Here, the predetermined time may be 10 minutes to 1 hour. The predetermined time may be adjusted by the driver 2.

The measuring step (S120) is a step of the measurement unit 12 measuring a biometric signal of the driver 2 for a predetermined time $\Delta t$ from the time when the stimulus is outputted. The measurement unit 12 may be configured as a GSR measurement device installed at the steering wheel 3.

As shown in FIG. 4B, the predetermined time $\Delta t$ is a time for which a biometric signal is principally changed due to a stimulus. The predetermined time $\Delta t$ may be about 5 to 10 seconds.

FIG. 4A is a graph showing a galvanic skin response measured when a stimulus is applied to a subject in a drowsy state. As shown in FIG. 4A, a change in current that appears in the skin of the subject when a stimulus is applied when the subject is in a drowsy state slowly decreases for the predetermined time $\Delta t$.

FIG. 4B is a graph showing a galvanic skin response measured when a stimulus is applied to a subject in an aroused state. As shown in FIG. 4B, a change in current that appears in the skin of the subject when a stimulus is applied when the subject is in an aroused state abruptly increases for the predetermined time $\Delta t$, and then decreases.

As shown in FIG. 3, when the measuring step (S120) is completed, the determining step (S130) is commenced. The determining step (S130) is a step of determining whether the biometric signal of the driver 2 is a response to the stimulus.

The controller 13 stores determination reference information used to determine whether the biometric signal of the driver 2 is a response to the stimulus. The determination reference information includes first determination reference information and second determination reference information.

The first determination reference information refers to a biometric signal measured when the stimulus is applied when the driver 2 is in an aroused state. The second determination reference information means a biometric signal measured when the stimulus is applied when the driver 2 is in a drowsy state. That is, the first determination reference information includes the galvanic skin response information of FIG. 4B. The second determination reference information includes the galvanic skin response information of FIG. 4A.

As shown in FIG. 3, at the determining step (S130), the controller 13 compares similarities between the measured biometric signal and the determination reference information in order to determine whether the biometric signal indicates a drowsy state or an aroused state. At the determining step (S130), the controller 13 may compare similarities between the measured biometric signal graph and the determination reference information graph.

In the case in which the similarities between the measured biometric signal and the first determination reference information are high, the controller 13 determines that the biometric signal of the driver 2 is a response to the stimulus. That is, the controller 13 determines that the biometric signal of the driver 2 indicates an aroused state.

In the case in which the similarities between the measured biometric signal and the second determination reference information are high, the controller 13 determines that the biometric signal of the driver 2 is not a response to the stimulus. That is, the controller 13 determines that the biometric signal of the driver 2 indicates a drowsy state.

As shown in FIG. 3, upon determining at the determining step (S130) that the biometric signal of the driver 2 is a response to the stimulus, the stimulating step (S110) is performed after a predetermined time. Here, the predetermined time may be 10 minutes to 1 hour. The predetermined time may be adjusted by the driver 2.

Upon determining at the determining step (S130) that the biometric signal of the driver 2 is not a response to the stimulus, the stimulating step (S110) is immediately reperformed. That is, the sensory organ of the driver 2 is stimulated again (S110), a biometric signal of the driver 2 is measured from the time when the stimulus is outputted (S120), and it is determined whether the biometric signal of the driver 2 is a response to the stimulus (S130).

The above process continues until it is determined at the determining step (S130) that the biometric signal of the driver 2 is a response to the stimulus. That is, the stimulation unit 11 continuously outputs the stimulus in order to stimulate the sensory organ of the driver 2 until it is determined that the state of the driver 2 has changed to an aroused state.

Upon determining at the determining step (S130) that a response pattern to the stimulus does not appear in the measured biometric signal of the driver 2, an autonomous driving level of the vehicle 1 may be increased. The autonomous driving level may be divided into level 0 to level 5 (based on the classification of Society of Automotive Engineers). Level 5 refers to a completely autonomous driving level. Level 2 refers to a driving assistance level. Level 4 is a level at which autonomous driving is possible without intervention of the driver 2. In this case, however, the driver 2 must intervene in a dangerous situation.

For example, in the case in which the autonomous driving level is level 1, upon determining at the determining step (S130) that a response pattern to the stimulus does not appear in the measured biometric signal of the driver 2, the autonomous driving level of the vehicle 1 may be increased to one of levels 2 to 5. In the case in which the autonomous driving level is increased, an accident of the vehicle 1 may be prevented before the state of the driver 2 is changed from a drowsy state to an aroused state. Subsequently, upon determining that the state of the driver 2 has changed to an aroused state, the autonomous driving level of the vehicle 1 may be decreased to the original state thereof.

Figure 5:
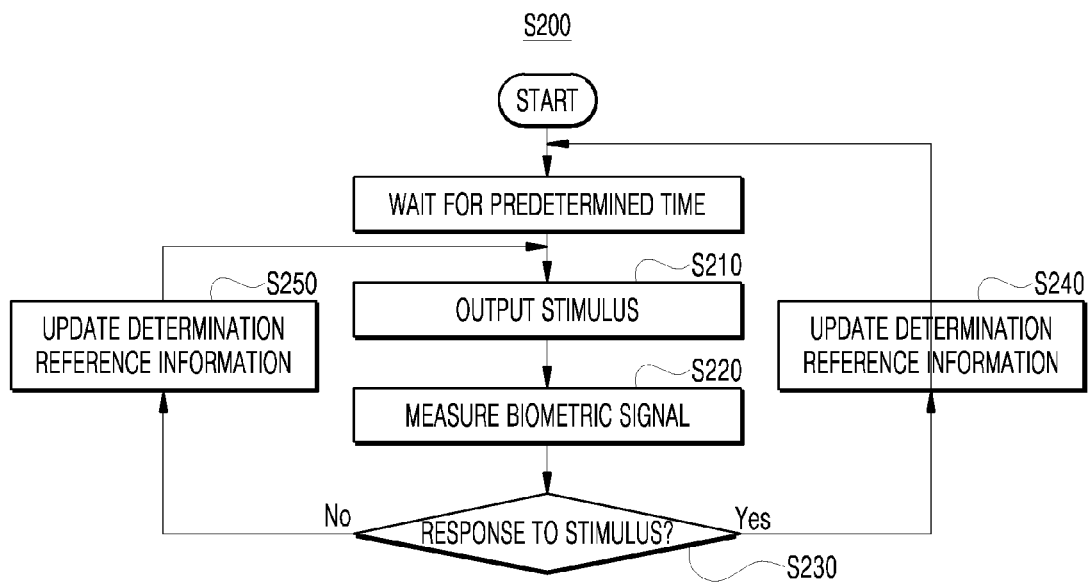
FIG. 5 is a flowchart showing a drowsy-driving prevention method according to a second embodiment of the present disclosure.

FIG. 5 is a flowchart showing a drowsy-driving prevention method (S200) according to a second embodiment of the present disclosure.

As shown in FIG. 5, the drowsy-driving prevention method (S200) according to the second embodiment of the present disclosure may include a stimulating step (S210), a measuring step (S220), a determining step (S230), and an updating step (S240 and S250).

The stimulating step (S210), the measuring step (S220), and the determining step (S230) of the second embodiment of the present disclosure are substantially identical to the stimulating step (S110), the measuring step (S120), and the determining step (S130) of the first embodiment of the present disclosure. Hereinafter, therefore, the stimulating step (S210), the measuring step (S220), and the determining step (S230) will be described briefly.

When the determining step (S230) is completed, the updating step (S240 and S250) is performed. The updating step (S240 and S250) is a step of updating determination reference information. The determination reference information is updated so as to include the information determined at the determining step (S230).

The information determined at the determining step (S230) includes information determining that similarities between the measured biometric signal and the first determination reference information are high (hereinafter referred to as "first information") and information determining that similarities between the measured biometric signal and the second determination reference information are high (hereinafter referred to as "second information").

As shown in FIG. 5, at the updating step (S240 and S250), the determination reference information is updated so as to include the first information and the second information. The updating step (S240 and S250) includes a first step (S240) and a second step (S250).

The first step (S240) is a step of updating the determination reference information so as to include the first information. When the first step (S240) is completed, the stimulating step (S210) is performed after a predetermined time. Here, the predetermined time may be 10 minutes to 1 hour. The predetermined time may be adjusted by the driver 2.

The second step (S250) is a step of updating the determination reference information so as to include the second information. When the second step (S250) is completed, the stimulating step (S210) is immediately reperformed.

The above process continues until it is determined at the determining step (S230) that the biometric signal of the driver 2 is a response to the stimulus. That is, the stimulation unit 11 continuously outputs stimuli in order to stimulate the sensory organ of the driver 2 until it is determined that the state of the driver 2 has changed to an aroused state.

At a producing step of the drowsy-driving prevention system 10 according to the embodiment of the present disclosure, basic determination reference information may be stored in the controller 13. The basic determination reference information may be information about galvanic skin responses measured after stimuli are applied to a limited number of subjects.

However, biometric signals, such as body temperature, heart rate, and GSR, are information that shows deviation between individuals. Consequently, there is deviation in similarities between the basic determination reference information, stored in the controller 13 at the producing step, and the biometric signals for each user.

In the drowsy-driving prevention method (S200) according to the second embodiment of the present disclosure, the basic determination reference information is updated through information including the user's own biometric information (the first information and the second information) at the time of driving the vehicle 1. As the number of times that the user uses the drowsy-driving prevention system 10 increases, therefore, the accuracy of determination at the determining step (S230) increases.

The first information and the second information generated most recently at the updating step (S240 and S250) may be transmitted to an administration server over a network. The administration server may store previous determination reference information. The previous determination reference information stored in the administration server is updated so as to include the first information and the second information generated most recently. The administration server feeds back update information of the first information and the second information to the drowsy-driving prevention system 10 over the network.

The administration server may be a database server that provides big data necessary to apply various artificial intelligence algorithms and data necessary to operate the drowsy-driving prevention system 10.

Artificial intelligence (AI) is an area of computer engineering science and information technology that studies methods to make computers mimic intelligent human behaviors such as reasoning, learning, self-improving, and the like.

In addition, artificial intelligence does not exist on its own, but is rather directly or indirectly related to a number of other fields in computer science. In recent years, there have been numerous attempts to introduce an element of AI into various fields of information technology to solve problems in the respective fields.

Machine learning is an area of artificial intelligence that includes the field of study that gives computers the capability to learn without being explicitly programmed More specifically, machine learning is a technology that investigates and builds systems, and algorithms for such systems, which are capable of learning, making predictions, and enhancing their own performance on the basis of experiential data. Machine learning algorithms, rather than only executing rigidly set static program commands, may be used to take an approach that builds models for deriving predictions and decisions from inputted data.

The network may function to connect the drowsy-driving prevention system 10 and the administration server to each other. The network may include a wireless network, such as wireless LANs, CDMA, or satellite communication, but the present disclosure is not limited thereto. In addition, the network may transmit and receive information using long distance communication. Here, the long distance communication may include code division multiple access (CDMA), frequency division multiple access (FDMA), time division multiple access (TDMA), orthogonal frequency division multiple access (OFDMA), or single carrier frequency division multiple access (SC-FDMA) technology.

The network may include connection of network elements such as hubs, bridges, routers, switches, and gateways. The network may include one or more connected networks, including a public network such as the Internet and a private network such as a secure corporate private network. For example, the network may include a multi-network environment. Access to the network may be provided via one or more wired or wireless access networks. Further, the network may support 5G communication and/or an Internet of things (IoT) network for exchanging and processing information between distributed components such as objects.

As shown in FIG. 1, the drowsy-driving prevention system 10 according to the embodiment of the present disclosure may include a communication unit 16.

The communication unit 16 may provide a communication interface necessary to provide a signal transmitted and received between the drowsy-driving prevention system 10 and a server 400 in the form of packet data in cooperation with the network. In addition, the communication unit 16 may support various kinds of object intelligence communications (such as Internet of things (IoT), Internet of everything (IoE), and Internet of small things (IoST)) and may support communications such as machine to machine (M2M) communication, vehicle to everything communication (V2X), and device to device (D2D) communication.

Figure 6:
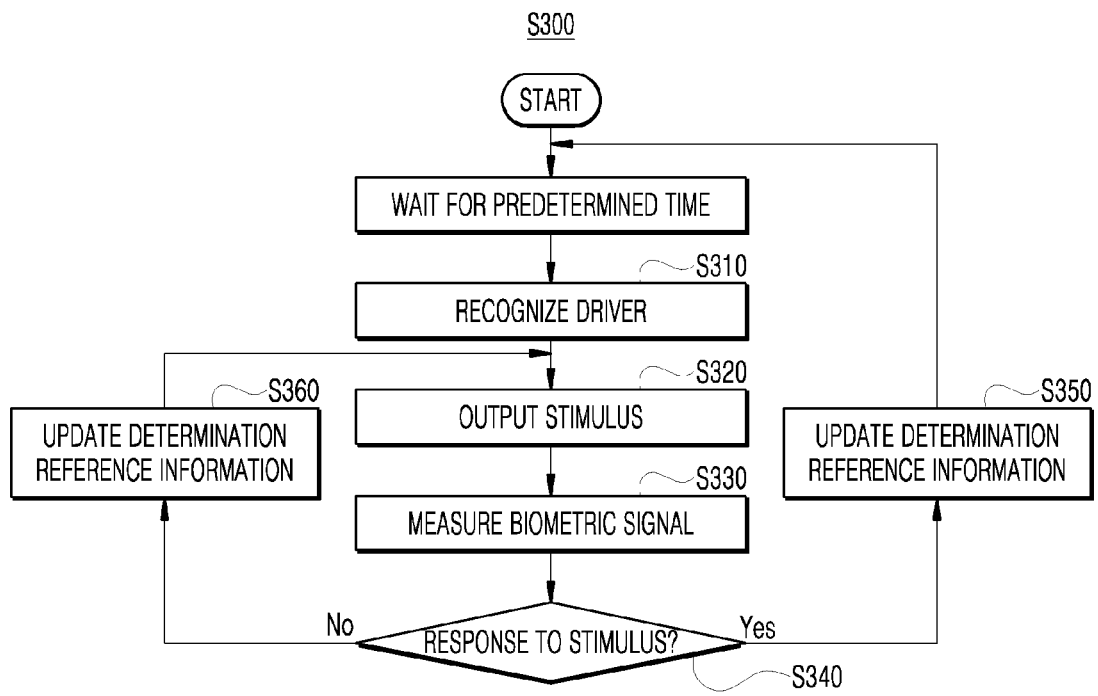
FIG. 6 is a flowchart showing a drowsy-driving prevention method according to a third embodiment of the present disclosure.

FIG. 6 is a flowchart showing a drowsy-driving prevention method (S300) according to a third embodiment of the present disclosure.

As shown in FIG. 6, the drowsy-driving prevention method (S300) according to the third embodiment of the present disclosure may include a recognizing step (S310), a stimulating step (S320), a measuring step (S330), a determining step (S340), and an updating step (S350 and S360).

As shown in FIG. 1, the drowsy-driving prevention system 10 according to the embodiment of the present disclosure includes a stimulation unit 11, a measurement unit 12, a capture unit 14, and a controller 13. The capture unit 14 is an image capture device that captures an image of the driver 2.

The capture unit 14 is provided in the vehicle 1. The capture unit 14 continuously or periodically captures images of the driver 2 while the vehicle 1 is being driven. The capture unit 14 may capture an image of the face of the driver 2.

The recognizing step (S310) is a step of analyzing the image captured by the capture unit 14 in order to recognize the driver 2. Face recognition technology is disclosed in Korean Patent Application Publication No. 2014-0087607, and therefore a detailed description thereof will be omitted.

When the recognizing step (S310) is completed, the stimulating step (S320), the measuring step (S330), and the determining step (S340) are sequentially performed. The stimulating step (S320) and the measuring step (S330) of the third embodiment of the present disclosure are substantially identical to the stimulating step (S110) and the measuring step (S120) of the first embodiment of the present disclosure. Hereinafter, therefore, the stimulating step (S320) and the measuring step (S330) will be described briefly.

As shown in FIG. 6, when the measuring step (S330) is completed, the determining step (S340) is commenced. The determining step (S340) is a step of determining whether the biometric signal of the driver 2 is a response to the stimulus.

The controller 13 stores determination reference information used to determine whether the biometric signal of the driver 2 is a response to the stimulus, for each driver. At the determining step (S340), the controller 13 loads the determination reference information of the driver 2 recognized at the recognizing step (S310). Subsequently, the controller 13 compares similarities between the measured biometric signal and the determination reference information in order to determine whether the biometric signal indicates a drowsy state or an aroused state.

When the determining step (S340) is completed, the updating step (S350 and S360) is performed. The updating step (S350 and S360) is a step of updating determination reference information for respective drivers. At the updating step (S350 and S360), the controller 13 loads the determination reference information of the driver 2 recognized at the recognizing step (S310). Subsequently, the determination reference information is updated so as to include the information determined at the determining step (S340).

As shown in FIG. 6, at the updating step (S350 and S360), the determination reference information for each driver is updated so as to include the first information and the second information. The updating step (S350 and S360) includes a first step (S350) and a second step (S360).

The first step (S350) is a step of updating the determination reference information for each driver so as to include the first information. When the first step (S350) is completed, the stimulating step (S320) is performed after a predetermined time.

The driver 2 may change during the predetermined time. After the predetermined time, therefore, the recognizing step (S310), the stimulating step (S320), the measuring step (S330), the determining step (S340), and the updating step (S350 and S360) are reperformed.

The second step (S360) is a step of updating the determination reference information for respective drivers so as to include the second information. When the second step (S360) is completed, the stimulating step (S320) is immediately reperformed.

The above process continues until it is determined at the determining step (S340) that the biometric signal of the driver 2 is a response to the stimulus. That is, the stimulation unit 11 continuously outputs the stimulus in order to stimulate the sensory organ of the driver 2 until it is determined that the state of the driver 2 has changed to an aroused state.

Biometric signals, such as body temperature, heart rate, and GSR, are information that shows deviation between individuals. Consequently, there is deviation in similarities between the basic determination reference information, stored in the controller 13 at the production step, and the biometric signals for each user.

In the drowsy-driving prevention method (S300) according to the third embodiment of the present disclosure, the driver 2 is automatically recognized at the time of driving the vehicle 1, and the determination reference information is updated for respective drivers. Even in the case in which the vehicle 1 is a shared vehicle, therefore, the accuracy of determination at the determining step (S340) increases as the number of times that a plurality of users uses the drowsy-driving prevention system 10 increases.

Figure 7:
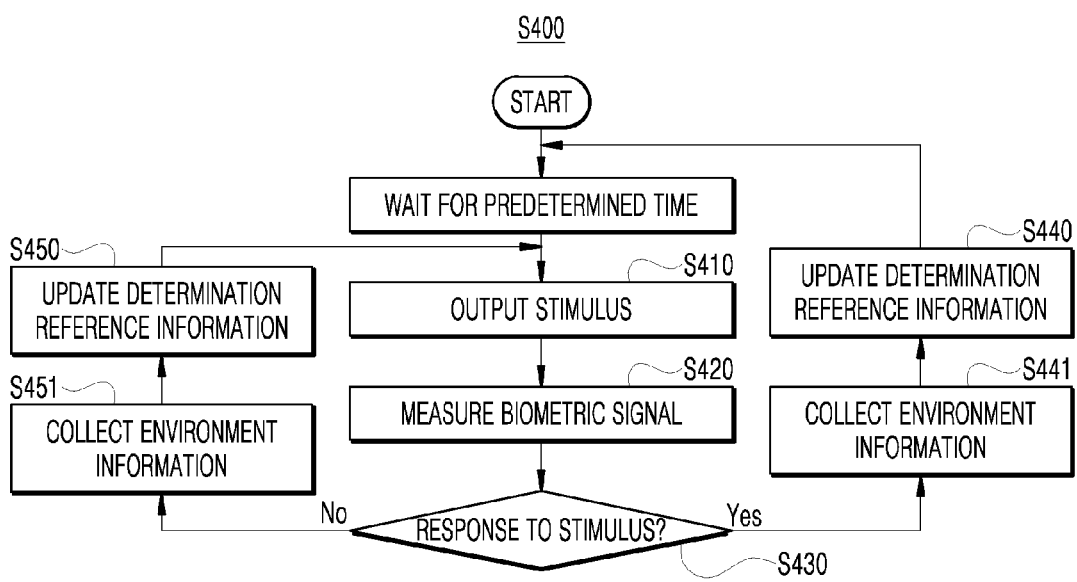
FIG. 7 is a flowchart showing a drowsy-driving prevention method according to a fourth embodiment of the present disclosure.

FIG. 7 is a flowchart showing a drowsy-driving prevention method (S400) according to a fourth embodiment of the present disclosure.

As shown in FIG. 7, the drowsy-driving prevention method (S400) according to the fourth embodiment of the present disclosure may include a stimulating step (S410), a measuring step (S420), a determining step (S430), and an updating step (S440 and S450).

As shown in FIG. 1, the drowsy-driving prevention system 10 according to the embodiment of the present disclosure includes a stimulation unit 11, a measurement unit 12, a measurement sensor 15, and a controller 13.

At least one measurement sensor 15 selected from among an illuminance sensor, a temperature sensor, and a carbon dioxide sensor is provided in the interior of the vehicle 1. The measurement sensor 15 is provided in the vehicle 1. The measurement sensor 15 continuously or periodically measures at least one of illuminance, temperature, or carbon dioxide while the vehicle 1 is being driven.

The stimulating step (S410), the measuring step (S420), and the determining step (S430) of the fourth embodiment of the present disclosure are substantially identical to the stimulating step (S210), the measuring step (S220), and the determining step (S230) of the second embodiment of the present disclosure. Hereinafter, therefore, the stimulating step (S410), the measuring step (S420), and the determining step (S430) will be described briefly.

When the determining step (S430) is completed, the updating step (S440 and S450) is performed. The updating step (S440 and S450) is a step of updating determination reference information. The determination reference information is updated so as to include the information determined at the determining step (S430) and information measured by the measurement sensor 15 (hereinafter referred to as "environment information") (S441 and S451).

The temperature in the vehicle 1 may affect the degree of arousal of the driver 2. That is, in the case in which the temperature in the vehicle 1 is high, the degree of arousal of the driver 2 may be low. The illuminance in the vehicle 1 may also affect the degree of arousal of the driver 2. That is, in the case in which the illuminance in the vehicle 1 is high, the degree of arousal of the driver 2 may be low.

The amount of carbon dioxide in the vehicle 1 may be a factor that determines the degree of arousal of the driver 2. A carbon dioxide sensor or a $CO_2$ sensor is a device for measuring carbon dioxide. A non-dispersive infrared (NDIR) method is a method of calculating the concentration of a specific component using the fact that a gaseous material, such as CO or $CO_2$, has a specific absorption spectrum for infrared light. In this method, infrared light having a frequency that is absorbed by carbon dioxide is emitted, and the amount of the infrared light that is detected without being absorbed by carbon dioxide molecules is measured.

As shown in FIG. 1, the environment information may include traffic information (navigation information). The traffic may affect the degree of arousal of the driver 2. That is, in the case in which the traffic is congested, the degree of arousal of the driver 2 may be high.

The information determined at the determining step (S430) includes information determining that similarities between the measured biometric signal and the first determination reference information are high (first information) and information determining that similarities between the measured biometric signal and the second determination reference information are high (second information).

As shown in FIG. 7, at the updating step (S440 and S450), the determination reference information is updated so as to include the first information, the second information, and the environment information (S441 and S451). The updating step (S440 and S450) includes a first step (S440) and a second step (S450).

The first step (S440) is a step of updating the determination reference information so as to include the first information and the environment information (S441). When the first step (S440) is completed, the stimulating step (S410) is performed after a predetermined time. Here, the predetermined time may be 10 minutes to 1 hour. The predetermined time may be adjusted by the driver 2.

The second step (S450) is a step of updating the determination reference information so as to include the second information and the environment information (S451). When the second step (S450) is completed, the stimulating step (S410) is immediately reperformed.

The above process continues until it is determined at the determining step (S430) that the biometric signal of the driver 2 is a response to the stimulus. That is, the stimulation unit 11 continuously outputs the stimulus in order to stimulate the sensory organ of the driver 2 until it is determined that the state of the driver 2 has changed to an aroused state.

At the producing step of the drowsy-driving prevention system 10 according to the embodiment of the present disclosure, basic determination reference information may be stored in the controller 13. The basic determination reference information may be information about galvanic skin responses measured after stimuli are applied to a limited number of subjects.

However, biometric signals, such as body temperature, heart rate, and GSR, are information that shows deviation between individuals. In addition, for the same subject, there is deviation depending on the ambient temperature, the health state, and a change in the emotion of the subject when measurement is performed. Consequently, there is deviation in similarities between the basic determination reference information, stored in the controller 13 at the producing step, and the biometric signals for respective driving environments as well as for each user.

In the drowsy-driving prevention method (S400) according to the fourth embodiment of the present disclosure, the basic determination reference information is updated through the first information, the second information, and the environment information at the time of driving the vehicle 1. As the number of times that the user uses the drowsy-driving prevention system 10 increases, therefore, the accuracy of determination at the determining step (S430) increases.

Figure 8:
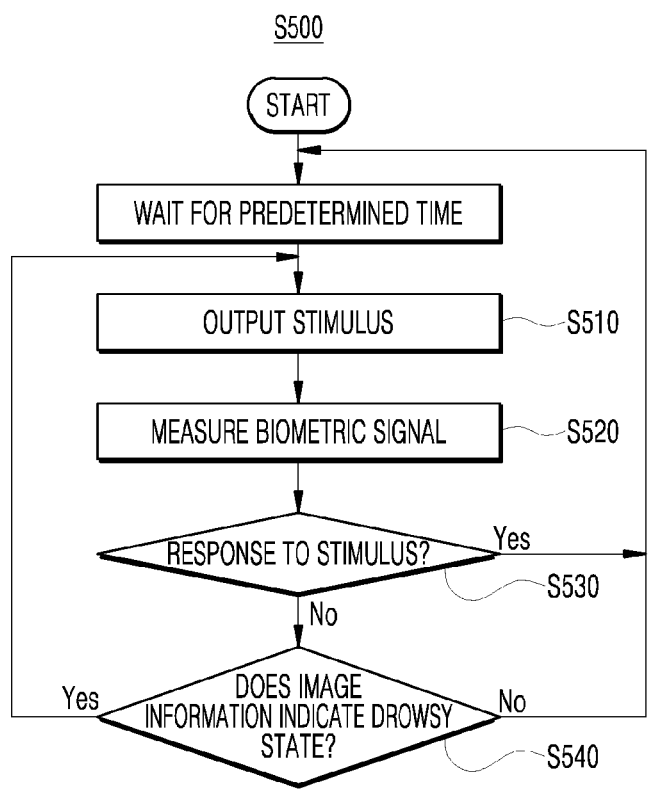
FIG. 8 is a flowchart showing a drowsy-driving prevention method according to a fifth embodiment of the present disclosure.

FIG. 8 is a flowchart showing a drowsy-driving prevention method (S500) according to a fifth embodiment of the present disclosure As shown in FIG. 8, the drowsy-driving prevention method (S500) according to the fifth embodiment of the present disclosure may include a stimulating step (S510), a measuring step (S520), a determining step (S530), and a confirming step (S540).

As shown in FIG. 1, the drowsy-driving prevention system 10 according to the embodiment of the present disclosure includes a stimulation unit 11, a measurement unit 12, a capture unit 14, and a controller 13. The capture unit 14 is an image capture device that captures an image of the driver 2.

The capture unit 14 is provided in the vehicle 1. The capture unit 14 continuously or periodically captures images of the driver 2 while the vehicle 1 is driven. The capture unit 14 may capture an image of the face or eyes of the driver 2.

The stimulating step (S510), the measuring step (S520), and the determining step (S530) of the fifth embodiment of the present disclosure are substantially identical to the stimulating step (S110), the measuring step (S120), and the determining step (S130) of the first embodiment of the present disclosure. Hereinafter, therefore, the stimulating step (S510), the measuring step (S520), and the determining step (S530) will be described briefly.

As shown in FIG. 8, when the measuring step (S520) is completed, the determining step (S530) is commenced. The determining step (S530) is a step of determining whether the biometric signal of the driver 2 is a response to the stimulus.

The controller 13 stores determination reference information used to determine whether the biometric signal of the driver 2 is a response to the stimulus. The determination reference information includes first determination reference information and second determination reference information.

The first determination reference information means a biometric signal measured when the stimulus is applied when the driver 2 is in an aroused state. The second determination reference information means a biometric signal measured when the stimulus is applied when the driver 2 is in a drowsy state. That is, the first determination reference information includes the galvanic skin response information of FIG. 4B. The second determination reference information includes the galvanic skin response information of FIG. 4A.

At the determining step (S530), the controller 13 compares similarities between the measured biometric signal and the determination reference information in order to determine whether the biometric signal indicates a drowsy state or an aroused state. At the determining step (S530), the controller 13 may compare similarities between the measured biometric signal graph and the determination reference information graph.

In the case in which the similarities between the measured biometric signal and the first determination reference information are high, the controller 13 determines that the biometric signal of the driver 2 is a response to the stimulus. That is, the controller 13 determines that the biometric signal of the driver 2 indicates an aroused state.

In the case in which the similarities between the measured biometric signal and the second determination reference information are high, the controller 13 determines that the biometric signal of the driver 2 is not a response to the stimulus. That is, the controller 13 determines that the biometric signal of the driver 2 indicates a drowsy state.

As shown in FIG. 8, upon determining at the determining step (S530) that the biometric signal of the driver 2 is a response to the stimulus, the stimulating step (S510) is performed after a predetermined time. Here, the predetermined time may be 10 minutes to 1 hour. The predetermined time may be adjusted by the driver 2.

Upon determining at the determining step (S530) that the biometric signal of the driver 2 is not a response to the stimulus, the confirming step (S540) is performed. The confirming step (S540) is a step of analyzing the image captured by the capture unit 14 in order to confirm whether the driver 2 is performing drowsy driving.

At the confirming step (S540), the controller 13 may analyze a captured image of the face or eyes of the driver 2 in order to confirm whether the driver 2 is performing drowsy driving. Technology for analyzing a captured image of the face or eyes of the driver 2 in order to confirm whether the driver 2 is performing drowsy driving is disclosed in Korean Patent Application Publication No. 2018-0056231 and in Korean Patent Registration No. 1795188, and therefore a detailed description thereof will be omitted.

As shown in FIG. 8, upon determining at the confirming step (S540) that the driver 2 is not performing drowsy driving, the stimulating step (S510) is performed after a predetermined time. Here, the predetermined time may be 10 minutes to 1 hour. The predetermined time may be adjusted by the driver 2.

Upon determining at the confirming step (S540) that the driver 2 is performing drowsy driving, the stimulating step (S510) is immediately reperformed. The above process continues until it is determined at the determining step (S530) that the biometric signal of the driver 2 is a response to the stimulus, or until it is determined at the confirming step (S540) that the biometric signal of the driver 2 indicates an aroused state. That is, the stimulation unit 11 continuously outputs the stimulus in order to stimulate the sensory organ of the driver 2 until it is determined or confirmed that the state if the driver 2 has changed to an aroused state.

Figure 9:
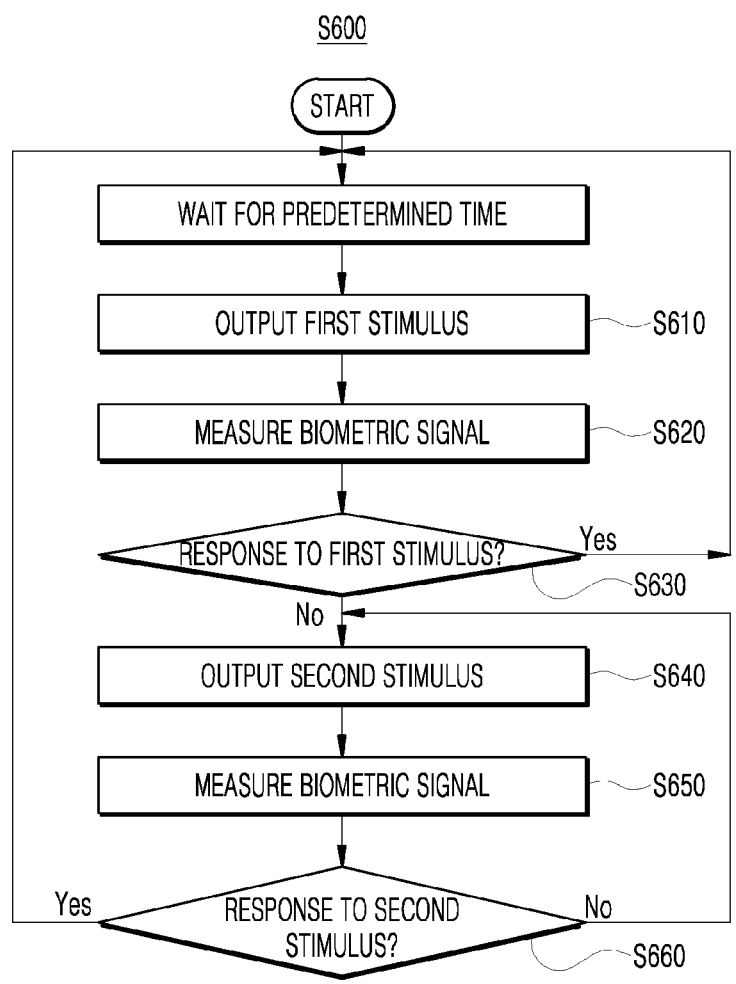
FIG. 9 is a flowchart showing a drowsy-driving prevention method according to a sixth embodiment of the present disclosure.

FIG. 9 is a flowchart showing a drowsy-driving prevention method (S600) according to a sixth embodiment of the present disclosure.

As shown in FIG. 9, the drowsy-driving prevention method (S600) according to the sixth embodiment of the present disclosure may include a first stimulating step (S610), a first measuring step (S620), a first determining step (S630), a second stimulating step (S640), a second measuring step (S650), and a second determining step (S660).

The first stimulating step (S610) is a step of the stimulation unit 11 outputting a first stimulus in order to stimulate the sensory organ of the driver 2. The first stimulating step (S610) is automatically commenced a predetermined time after the vehicle 1 is started. Here, the predetermined time may be 10 minutes to 1 hour. The predetermined time may be adjusted by the driver 2.

The first measuring step (S620) is a step of the measurement unit 12 measuring a biometric signal of the driver 2 for a predetermined time $\Delta t$ from the time when the first stimulus is outputted. As shown in FIG. 4B, the predetermined time $\Delta t$ is a time for which a biometric signal is principally changed due to a stimulus. The predetermined time $\Delta t$ may be about 5 to 10 seconds.

As shown in FIG. 9, when the first measuring step (S620) is completed, the first determining step (S630) is commenced. The first determining step (S630) is a step of determining whether the biometric signal of the driver 2 is a response to the first stimulus.

The controller 13 stores determination reference information used to determine whether the biometric signal of the driver 2 is a response to the first stimulus. The determination reference information includes first determination reference information and second determination reference information.

The first determination reference information refers to a biometric signal measured when the first stimulus is applied when the driver 2 is in an aroused state. The second determination reference information means a biometric signal measured when the first stimulus is applied when the driver 2 is in a drowsy state. That is, the first determination reference information includes the galvanic skin response information of FIG. 4B. The second determination reference information includes the galvanic skin response information of FIG. 4A.

At the first determining step (S630), the controller 13 compares similarities between the measured biometric signal and the determination reference information in order to determine whether the biometric signal indicates a drowsy state or an aroused state. At the first determining step (S630), the controller 13 may compare similarities between the measured biometric signal graph and the determination reference information graph.

In the case in which the similarities between the measured biometric signal and the first determination reference information are high, the controller 13 determines that the biometric signal of the driver 2 is a response to the first stimulus. That is, the controller 13 determines that the biometric signal of the driver 2 indicates an aroused state.

In the case in which the similarities between the measured biometric signal and the second determination reference information are high, the controller 13 determines that the biometric signal of the driver 2 is not a response to the first stimulus. That is, the controller 13 determines that the biometric signal of the driver 2 is a drowsy state.

As shown in FIG. 9, upon determining at the first determining step (S630) that the biometric signal of the driver 2 is a response to the first stimulus, the first stimulating step (S610) is performed after a predetermined time. Here, the predetermined time may be 10 minutes to 1 hour. The predetermined time may be adjusted by the driver 2.

Upon determining at the first determining step (S630) that the biometric signal of the driver 2 is not a response to the first stimulus, the second stimulating step (S640) is performed. The second stimulating step (S640) is a step of the stimulation unit 11 outputting a second stimulus in order to stimulate the sensory organ of the driver 2.

The first stimulus and the second stimulus may stimulate different sensory organs of the driver 2. That is, in the case in which the first stimulus is a vibratory stimulus, the second stimulus may be a visual stimulus (a video device), an auditory stimulus (an audio device), or an olfactory stimulus (an aromatic device).

In addition, the second stimulus may stimulate the same sensory organ of the driver 2 with higher intensity than the first stimulus. That is, in the case in which the first stimulus is a vibratory stimulus, the second stimulus may be a vibratory stimulus having a higher vibration level than the first stimulus.

In the case in which the first stimulus is an auditory stimulus, the second stimulus may be an auditory stimulus having a higher decibel level than the first stimulus. In the case in which the first stimulus is a visual stimulus, the second stimulus may be a visual stimulus that is clearer or more stimulating than the first stimulus.

As a stimulus is repeatedly applied, the degree of a response to the stimulus gradually decreases. An action of becoming insensitive to the repeated stimulus is called habituation. In the case in which the first stimulus and the second stimulus stimulate different sensory organs of the driver 2, or in the case in which the second stimulus is stronger than the first stimulus, habituation is prevented, whereby a rapid change of the state of the driver 2 to an aroused state is possible.

The second measuring step (S650) is a step of the measurement unit 12 measuring a biometric signal of the driver 2 for a predetermined time $\Delta t$ from the time when the second stimulus is outputted. As shown in FIG. 4B, the predetermined time $\Delta t$ is a time for which a biometric signal is principally changed due to a stimulus. The predetermined time $\Delta t$ may be about 5 to 10 seconds.

As shown in FIG. 9, when the second measuring step (S650) is completed, the second determining step (S660) is commenced. The second determining step (S660) is a step of determining whether the biometric signal of the driver 2 is a response to the second stimulus.

The controller 13 stores determination reference information used to determine whether the biometric signal of the driver 2 is a response to the second stimulus. The determination reference information includes first determination reference information and second determination reference information.

In the case in which the similarities between the measured biometric signal and the first determination reference information are high, the controller 13 determines that the biometric signal of the driver 2 is a response to the second stimulus. That is, the controller 13 determines that the biometric signal of the driver 2 indicates an aroused state.

In the case in which the similarities between the measured biometric signal and the second determination reference information are high, the controller 13 determines that the biometric signal of the driver 2 is not a response to the second stimulus. That is, the controller 13 determines that the biometric signal of the driver 2 indicates a drowsy state.

As shown in FIG. 9, upon determining at the second determining step (S660) that the biometric signal of the driver 2 is a response to the first second stimulus, the first stimulating step (S610) is performed after a predetermined time. Here, the predetermined time may be 10 minutes to 1 hour. The predetermined time may be adjusted by the driver 2.

Upon determining at the second determining step (S660) that the biometric signal of the driver 2 is not a response to the second stimulus, the second stimulating step (S640) is immediately reperformed. The above process continues until it is determined at the second determining step (S660) that the biometric signal of the driver 2 is a response to the stimulus. That is, the stimulation unit 11 continuously outputs the stimulus in order to stimulate the sensory organ of the driver 2 until it is determined that the state of the driver 2 has been changed to an aroused state.

Meanwhile, in the case in which the driver 2 falls into a deep sleep during driving due to overwork, for example, a change to an aroused state may not be easy through a uniform stimulus.

Figure 10:
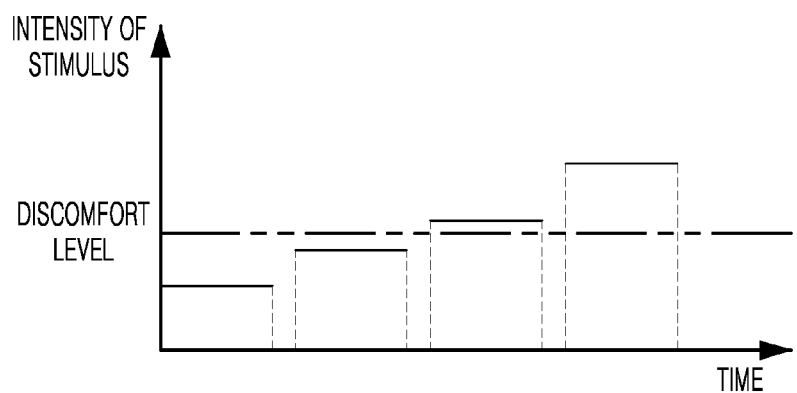
FIG. 10 is a graph showing the state in which the intensity of a second stimulus is changed whenever a second stimulating step of the drowsy-driving prevention method of FIG. 9 is reperformed.

FIG. 10 is a graph showing the state in which the intensity of the second stimulus is changed whenever the second stimulating step (S640) of the drowsy-driving prevention method (S600) of FIG. 9 is reperformed.

As shown in FIG. 10, the intensity of the second stimulus may be changed whenever the second stimulating step (S640) is reperformed. Preferably, the intensity of the second stimulus is increased whenever the second stimulating step (S640) is reperformed.

Response to a stimulus is subjective for each individual. In the case in which the intensity of the stimulus is increased to a predetermined level, however, the probability of the stimulus causing discomfort may become high. In the case in which the intensity of the second stimulus is increased whenever the second stimulating step (S640) is reperformed, habituation to the repeated stimulus may be prevented, and discomfort may be caused, whereby a rapid change to an aroused state may be possible.

Figure 11:
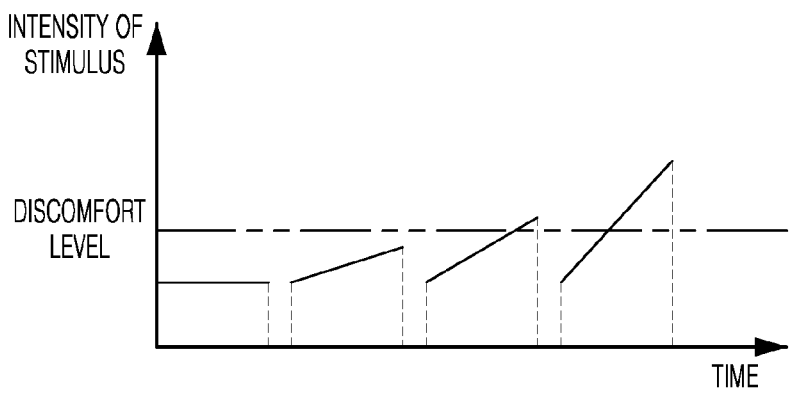
FIG. 11 is a graph showing the state in which the intensity and pattern of the second stimulus are changed whenever the second stimulating step of the drowsy-driving prevention method of FIG. 9 is reperformed.

FIG. 11 is a graph showing the state in which the intensity and pattern of the second stimulus are changed whenever the second stimulating step (S640) of the drowsy-driving prevention method (S600) of FIG. 9 is reperformed.

As shown in FIG. 11, the intensity and pattern of the second stimulus may be changed whenever the second stimulating step (S640) is reperformed. In the case in which the intensity and pattern of the second stimulus are changed whenever the second stimulating step (S640) is reperformed, habituation to the repeated stimulus may be prevented, and discomfort may be caused, whereby a rapid change to an aroused state may be possible.

The example embodiments described above may be implemented through computer programs executable through various components on a computer, and such computer programs may be recorded in computer-readable media. Examples of the computer-readable media include, but are not limited to: magnetic media such as hard disks, floppy disks, and magnetic tape; optical media such as CD-ROM disks and DVD-ROM disks; magneto-optical media such as floptical disks; and hardware devices that are specially configured to store and execute program codes, such as ROM, RAM, and flash memory devices.

The computer programs may be those specially designed and constructed for the purposes of the present disclosure or they may be of the kind well known and available to those skilled in the computer software arts. Examples of program code include both machine code, such as produced by a compiler, and higher level code that may be executed by the computer using an interpreter.

As used in the present application (especially in the appended claims), the terms 'a/an' and 'the' include both singular and plural references, unless the context clearly states otherwise. Also, it should be understood that any numerical range recited herein is intended to include all sub-ranges subsumed therein (unless expressly indicated otherwise) and therefore, the disclosed numeral ranges include every individual value between the minimum and maximum values of the numeral ranges.

Also, the order of individual steps in process claims of the present disclosure does not imply that the steps must be performed in this order; rather, the steps may be performed in any suitable order, unless expressly indicated otherwise. In other words, the present disclosure is not necessarily limited to the order in which the individual steps are recited. All examples described herein or the terms indicative thereof ("for example", etc.) used herein are merely to describe the present disclosure in greater detail. Therefore, it should be understood that the scope of the present disclosure is not limited to the example embodiments described above or by the use of such terms unless limited by the appended claims. Also, it should be apparent to those skilled in the art that various alterations, substitutions, and modifications may be made within the scope of the appended claims or equivalents thereof. It should be apparent to those skilled in the art that various substitutions, changes and modifications which are not exemplified herein but are still within the spirit and scope of the present disclosure may be made.

The present disclosure is thus not limited to the example embodiments described above, and rather intended to include the following appended claims, and all modifications, equivalents, and alternatives falling within the spirit and scope of the following claims.

What is claimed is:

1. A drowsy-driving prevention method in a vehicle having a stimulation unit configured to output a stimulus, a measurement unit configured to measure a biometric signal, a capture unit configured to capture an image of a driver, and a controller configured to control the stimulation unit, the measurement unit, and the capture unit, the drowsy-driving prevention method comprising:
   stimulating a sensory organ of the driver by outputting the stimulus, by the stimulation unit;
   measuring, by the measurement unit, a biometric signal of the driver from a time when the stimulus is outputted;
   determining whether the biometric signal of the driver is a response to the stimulus; and
   upon determining that the biometric signal of the driver is not a response to the stimulus, confirming whether the driver is performing drowsy driving by analyzing the image captured by the capture unit, wherein
   upon confirming that the driver is performing drowsy driving, the stimulating is reperformed.

2. The drowsy-driving prevention method according to claim 1, wherein
   the controller stores determination reference information used to determine whether the biometric signal of the driver is a response to the stimulus, and
   when the determining is completed, the determination reference information is updated so as to include information determined at the determining.

3. The drowsy-driving prevention method according to claim 2, wherein
   the drowsy-driving prevention method further comprises recognizing the driver by analyzing the image captured by the capture unit, and
   the determination reference information is updated for each driver.

4. The drowsy-driving prevention method according to claim 1, wherein the controller stores determination reference information used to determine whether the biometric signal of the driver is a response to the stimulus, at least one measurement sensor selected from among an illuminance sensor, a temperature sensor, and a carbon dioxide sensor is provided in an interior of the vehicle, and when the determining is completed, the determination reference information is updated so as to include information determined at the determining and information measured by the at least one measurement sensor.

5. The drowsy-driving prevention method according to claim 1, wherein, upon determining that the biometric signal of the driver is not a response to the stimulus, an autonomous driving level of the vehicle is increased.

* * * * *